United States Patent
Singh (10) Patent No.: US 9,927,411 B2
(45) Date of Patent: Mar. 27, 2018

(54) HUMIDITY AND SULFUR CONCENTRATION IN TEST CHAMBER

(71) Applicant: International Business Machines Corporation, Armonk, NY (US)

(72) Inventor: Prabjit Singh, Poughkeepsie, NY (US)

(73) Assignee: International Business Machines Corporation, Armonk, NY (US)

(*) Notice: Subject to any disclaimer, the term of this patent is extended or adjusted under 35 U.S.C. 154(b) by 255 days.

(21) Appl. No.: 14/847,043

(22) Filed: Sep. 8, 2015

(65) Prior Publication Data

US 2017/0067867 A1     Mar. 9, 2017

(51) Int. Cl.
*G01N 3/18*     (2006.01)
*G01N 33/00*    (2006.01)
*G01N 17/00*    (2006.01)

(52) U.S. Cl.
CPC ....... *G01N 33/0016* (2013.01); *G01N 17/002* (2013.01); *G01N 33/0073* (2013.01)

(58) Field of Classification Search
CPC ........ G01N 3/18; G01N 17/002; G01N 17/00; G01N 17/004; G01N 17/02; G01N 2203/0226; G01N 2203/0222
See application file for complete search history.

(56) References Cited

U.S. PATENT DOCUMENTS

| | | | | |
|---|---|---|---|---|
| 4,139,953 A | * | 2/1979 | Gaskell | F26B 13/08 34/216 |
| 4,192,323 A | * | 3/1980 | Horne | A24B 1/02 131/303 |
| 4,196,544 A | * | 4/1980 | Davis | A01G 7/045 165/47 |
| 4,572,427 A | * | 2/1986 | Selfridge | A01C 1/02 165/146 |
| H000229 H | * | 3/1987 | Phillips | 165/48.1 |
| 4,685,305 A | * | 8/1987 | Burg | A23B 7/148 165/282 |
| 4,701,415 A | * | 10/1987 | Dutton | B01L 1/00 435/286.6 |

(Continued)

FOREIGN PATENT DOCUMENTS

| | | | | |
|---|---|---|---|---|
| CN | 103217376 B | 6/2015 | | |
| EP | 1378248 A1 | * | 1/2004 | A61L 2/208 |

(Continued)

OTHER PUBLICATIONS

IBM: List of IBM Patents or Patent Applications Treated As Related (Appendix P), Feb. 11, 2016, 2 pages.

(Continued)

*Primary Examiner* — David A Rogers (74) *Attorney, Agent, or Firm* — Michael O'Keefe (57) ABSTRACT

A structure is provided. The structure may include an environmental test chamber including a sample chamber, a first air path beginning in the sample chamber and extending through a humidity control chamber, the first air path circulates air between the test chamber and the humidity control chamber, and a second air path beginning in the sample chamber and extending through a pollutant control chamber, the second air path circulates air between the test chamber and the pollutant control chamber.

14 Claims, 6 Drawing Sheets

(56) References Cited

U.S. PATENT DOCUMENTS

| | | | | |
|---|---|---|---|---|
| 4,711,131 | A * | 12/1987 | Hopkins | E21B 17/006 73/799 |
| 5,127,574 | A * | 7/1992 | Mosser | B05B 15/1222 118/309 |
| 5,381,701 | A * | 1/1995 | Frankenthal | G01R 31/2817 73/865.6 |
| 5,728,185 | A * | 3/1998 | Buchholz, Jr. | B05B 15/1233 118/326 |
| 6,113,262 | A * | 9/2000 | Purola | G01M 99/002 374/45 |
| 6,227,701 | B1 * | 5/2001 | Wu | G01R 31/2849 374/45 |
| 6,272,767 | B1 * | 8/2001 | Botruff | G01N 17/002 34/202 |
| 6,711,961 | B2 * | 3/2004 | Theriault | G01R 31/2849 73/865.6 |
| 6,978,226 | B2 * | 12/2005 | Kanehira | G01N 17/00 702/183 |
| 7,127,958 | B2 * | 10/2006 | Blewett | G01M 17/007 73/865.6 |
| 7,363,831 | B2 * | 4/2008 | Willemin | G01N 17/00 73/865.6 |
| 7,506,555 | B2 * | 3/2009 | Brostmeyer | G01M 15/14 73/150 R |
| 7,784,367 | B2 * | 8/2010 | Kojima | C09D 11/40 106/31.13 |
| 8,261,601 | B2 * | 9/2012 | Stolle | G01N 17/002 422/53 |
| 8,629,688 | B2 | 1/2014 | Chu et al. | |
| 8,763,480 | B2 * | 7/2014 | Shimada | G01N 25/68 73/73 |
| 8,927,289 | B2 | 1/2015 | Fujii et al. | |
| 9,677,987 | B2 * | 6/2017 | Campbell | G01N 15/0656 |
| 9,677,991 | B2 * | 6/2017 | Lehman | G01M 99/002 |
| 2002/0197867 | A1 * | 12/2002 | Kataoka | B01D 53/0407 438/689 |
| 2004/0141036 | A1 * | 7/2004 | Ishikawa | G01N 17/002 347/97 |
| 2007/0023536 | A1 | 2/2007 | Baston | |
| 2007/0051906 | A1 * | 3/2007 | Brennan | G01N 17/002 250/504 R |
| 2007/0089548 | A1 * | 4/2007 | Brostmeyer | G01M 15/14 73/866 |
| 2008/0236305 | A1 * | 10/2008 | Masset | G01N 17/002 73/865.6 |
| 2010/0009443 | A1 * | 1/2010 | Skinn | C12M 21/06 435/375 |
| 2011/0290043 | A1 * | 12/2011 | Lehman | G01M 99/002 73/865.6 |
| 2013/0283542 | A1 * | 10/2013 | Jenkins | C11D 17/046 8/137 |
| 2014/0111229 | A1 * | 4/2014 | Hamann | G01N 27/00 324/700 |
| 2014/0152449 | A1 * | 6/2014 | Klein | H05K 1/0268 340/662 |
| 2014/0314967 | A1 * | 10/2014 | Wu | C23C 22/60 427/560 |

FOREIGN PATENT DOCUMENTS

| | | | | |
|---|---|---|---|---|
| EP | 3032240 A1 * | 6/2016 | | G01N 17/002 |
| GB | 1326575 A * | 8/1973 | | F26B 21/06 |
| JP | 63229152 A * | 9/1988 | | |
| JP | 08304265 A | 11/1996 | | |
| WO | 9857321 A1 | 12/1998 | | |

OTHER PUBLICATIONS

Pending U.S. Appl. No. 15/041,072, filed Feb. 11, 2016, entitled: "Humidity and Sulfur Concentration in Test Chamber", 21 pages.
Abbott, "The Development and Performance Characteristics of Mixed Flowing Gas Test Environment", IEEE Transactions on Components, Hybrids, and Manufacturing Technology, vol. 11, No. 1, Mar. 1988, pp. 22-35.
Fu et al., "Testing Printed Circuit Boards for Creep Corrosion in Flowers of Sulfur Chamber", APEX2015, Abstract, pp. 1-12.
Chao et al., "Evaluation of a Mixed Flowing Gas Test", Abstract, 1991 IEEE, pp. 216-228.
Chiarenzelli, "Tarnishing Studies on Contact Materials", IEEE Transactions Onparts, Materials and Packaging, vol. PMP-3, No. 3, Sep. 1967, pp. 89-96.
Fu et al., "Creep Corrosion Test in Flowers of Sulfur Chamber", ICEP 2014 Proceedings, pp. 197-201.
Lee et al., "The Methodology to Monitor Gaseous Contamination in Data Centers", iMPACT, International Microsystems, Packaging, Assembly and Circuits Technology conference, 2013, Abstract, IEEE Catalog No. CFP1359B-ART, pp. 271-274.
iNEMI, "Statement of Work (SOW) iNEMI Board Assembly TIG Qualification Test Development for Creep Corrosion, Phase 1 (Primary Investigation of Flowers of Sulfur Test) Project", iNEMI International Electronics Manufacturing Initiative, Advancing manufacturing technology, Version # 1.3, Date: Feb. 18, 2013, pp. 1-8.
iNEMI, "Qualification Test for Creep Corrosion in Flowers of Sulfur Chamber: Phase 2 End of project webinar", iNEMI International Electronics Manufacturing Initiative, Advancing manufacturing technology, May 11, 2015, pp. 1-56.
Reagor et al., "Tarnishing of Silver by Sulfur Vapor: Film Characteristics and Humidity Effects", J. Electrochem. Soc.: Solid-State Science and Technology, vol. 128, No. 3, Mar. 1981, pp. 701-705.
Sinclair, "Tarnishing of Silver by Organic Sulfur Vapors: Rates and Film Characteristics", Abstract, J. Electrochem. Soc.: Electrochemical Science and Technology, Jan. 1982, pp. 33-40.
Vadimsky et al., "Ru and RuO2 as Electrical Contact Materials: Preparation and Environmental Interactions", Abstract, J. Electrochem. Soc.: Solid-State Science and Technology, Nov. 1979, pp. 2017-2023, Vo. 126, No. 11, Electrical Contact Materials.
Weeks, "Sulfur Corrosion of PCB Surface Finishes in Sulfur-Rich Environments", IPC 3-11g Committee Meeting, 2014 Western Digital Technologies, Inc., absolutely WD, pp. 1-35.
Wexler et al., "Relative Humidity-Temperature Relationships of Some Saturated Salt Solutions in the Temperature Range 0° to 50° C.[1]", Journal of Research of the National Bureau of Standards, vol. 53, No. 1, Jul. 1954, Research Paper 2512, pp. 19-26.

* cited by examiner

**Figure 6
Section A-A**

Figure 7

HUMIDITY AND SULFUR CONCENTRATION IN TEST CHAMBER

BACKGROUND

The present invention generally relates to humidity and sulfur concentration in an environmental test chamber, and more particularly to controlling a relative humidity independent of air temperature and controlling a sulfur concentration independent of air temperature.

An environment test chamber can be used to reproduce field environmental conditions and predict failures modes. The test results from an environmental test chamber can be used to improve the design of electronic components and improve the reliability of electronic components.

SUMMARY

According to an embodiment of the present invention, a method is provided. The method may include controlling a relative humidity in a sample chamber by circulating air sequentially from the sample chamber through a humidity control chamber and back to the sample chamber, and controlling a pollutant concentration in the sample chamber by circulating air sequentially from the sample chamber to a pollutant control chamber and back to the sample chamber.

According to an embodiment of the present invention, a structure is provided. The structure may include an environmental test chamber including a sample chamber, a first temperature control chamber coupled to the sample chamber, a humidity control chamber coupled to the first temperature control chamber, a second temperature control chamber coupled to the humidity control chamber, a first blower circulating air sequentially from the test chamber, through the first temperature control chamber, through the humidity control chamber, through the second temperature control chamber and back to the test chamber, a fourth temperature control chamber coupled to the sample chamber, a pollutant control chamber coupled to the fourth temperature control chamber, a third temperature control chamber coupled to the pollutant chamber, and a second blower circulating air sequentially from the test chamber, through the fourth temperature control chamber, through the pollutant control chamber, through the third temperature control chamber and back to the test chamber.

According to an embodiment of the present invention, a structure is provided. The structure may include an environmental test chamber including a sample chamber, a first air path beginning in the sample chamber and extending through a humidity control chamber, the first air path circulates air between the test chamber and the humidity control chamber, and a second air path beginning in the sample chamber and extending through a pollutant control chamber, the second air path circulates air between the test chamber and the pollutant control chamber.

BRIEF DESCRIPTION OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper", "lower", "right", "left", "vertical", "horizontal", "top", "bottom", and derivatives thereof shall relate to the disclosed structures and methods, as oriented in the drawing figures. The terms "overlying", "atop", "on top", "positioned on" or "positioned atop" mean that a first element, such as a first structure, is present on a second element, such as a second structure, wherein intervening elements, such as an interface structure may be present between the first element and the second element. The term "direct contact" means that a first element, such as a first structure, and a second element, such as a second structure, are connected without any intermediary conducting, insulating or semiconductor layers at the interface of the two elements.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is rather focused on the distinctive features or elements of various embodiments of the present invention.

An environment test chamber can be used to reproduce field environmental conditions and predict failures modes. For example, if a circuit board fails in the field and there is a certain failure mode or signature, such as creep corrosion, the environmental test chamber can be used to try to reproduce in the lab the same failure mechanism. Once a method to reproduce the certain failure is obtained in the environmental test chamber, other designs of the failing electronic component, such as the circuit board, can be tested. The test results can be used to improve the design of the circuit board and to reduce the incidence of creep corrosion failures in the field.

A mixed flowing gas (MFG) chamber is a type of environmental test chamber used for environmental testing, or testing, of a product, particularly an electronic product, to evaluate resistance to corrosion due to gases in the atmosphere. The MFG chamber provides accelerated corrosion testing and exposes the product to a mixture of pollutant gases in a controlled temperature and humidity environment. The MFG chamber controls several environmental attributes. The environmental attributes include temperature (° C.), relative humidity (% RH), concentration of gaseous pollutants (in parts per billion, ppb, or parts per million, ppm, level), and other variables such as a volume exchange rate and an airflow rate. Examples of the gaseous pollutants introduced into the MFG chamber can include hydrogen sulfide ($H_2S$), sulfur dioxide ($SO_2$), ozone ($O_3$), nitrogen dioxide ($NO_2$), chorine ($Cl_2$) and water ($H_2O$) for relative humidity. The purpose of the testing is to simulate corrosion due to atmospheric exposure. The MFG chamber exposes the product to a gas such as chlorine, hydrogen sulfide, nitrogen dioxide, ozone and sulfur dioxide at levels in the parts per billion range, in a controlled environmental chamber. The MFG chamber can be used to accelerate failure mechanisms seen during a products lifetime use in a particular environment such as an office, a light industrial, a moderate industrial, or a heavy industrial setting. The MFG chamber can be used to perform testing on a bare metal surface, a circuit board, a connector, a sub-assembly, a complete assembly and other products. In a raised floor configuration or environment, a typical computer datacenter may have a concentration of hydrogen sulfide ($H_2S$) less than 10 ppb, sulfur dioxide ($SO_2$) approximately 30-40 ppb, and chorine ($Cl_2$) less than 1 ppb.

In general, the MFG chamber can be expensive to build and difficult to maintain the gaseous pollutant composition and relative humidity. Most MFG chambers cannot reproduce a relative humidity greater than 75%. High humidity levels in MFG chamber may be necessary to reproduce creep corrosion.

Conventional flowers of sulfur chambers cannot control the sulfur concentration in the air independent of the air temperature.

An MFG chamber may be used to simulate a particular environment and test creep corrosion in electronic components. Creep corrosion is a mechanism where copper metallization on a circuit board is attacked by corrosive gases in a high moisture environment, for example in a data center. Copper lines on the circuit board can be attacked by hydrogen sulfide ($H_2S$) and forms copper sulfide ($Cu_2S$) corrosive product on the surface of a circuit board. The copper sulfide corrosive product spreads out and physically creeps across the surface of the circuit board and can bridge neighboring copper lines and copper features on the circuit board. The copper sulfide is a semiconductor. The copper sulfide corrosive product has impurities on the surface from the environment which increases its electrical conductivity. The copper sulfide corrosive product can form a short between the copper lines and features and damage the circuit board and other electronics which are connected to the circuit board.

The present invention generally relates to humidity and sulfur concentration in an environmental test chamber, and more particularly to controlling a relative humidity independent of air temperature and controlling a sulfur concentration independent of air temperature. One way to control the relative humidity and the sulfur concentration in an environmental test chamber independent of air temperature may include circulating the air and sequentially exposing it to a saturated salt at a predefined temperature followed by exposing it to sulfur at a predefined temperature. An embodiment by which to control the humidity and the sulfur concentration in an environmental test chamber independent of temperature is described in detail below by referring to the accompanying drawings in FIGS. 1 to 7.

Figure 1:
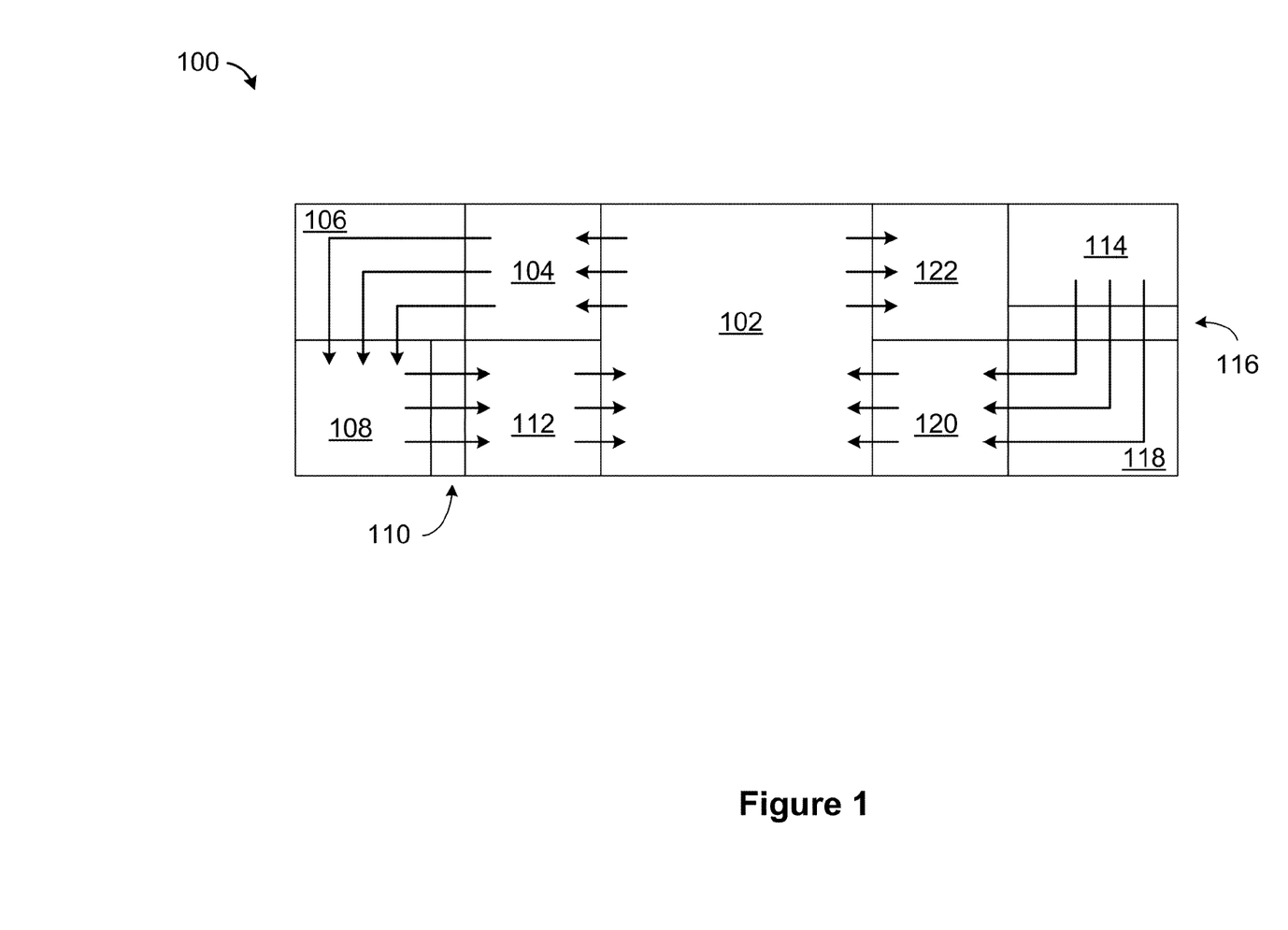
FIG. 1 is a cross-section view of an environmental test chamber, according to an exemplary embodiment.

Referring now to FIG. 1, an environmental test chamber 100 according to an exemplary embodiment is shown. The environmental test chamber 100 may include a sample chamber 102, a first temperature control chamber 104, a first blower 106, a humidity control chamber 108 containing a saturated salt solution, a first filter 110, a second temperature control chamber 112, a fourth temperature control chamber 122, a pollutant chamber 114 containing a bed of sulfur, a second filter 116, a second blower 118 and a third temperature control chamber 120. The arrows shown in FIG. 1 indicate an air circulation pattern through the environmental test chamber 100. Air continuously flows throughout the various chambers by way of the first blower 106 and the second blower 118. The continuous movement of air helps to achieve a desired temperature, a desired humidity and a desired pollutant concentration in the sample chamber 102. In an embodiment, the air may flow at a rate of 1 meter/second.

In an embodiment, the sample chamber 102 may be a cube made of acrylic with silicone grease coated rubber gaskets. For example, a sample chamber 102 with a volume of approximately 1 $m^3$ may be constructed of 12.7 mm (½") thick acrylic. A front face of the sample chamber 102 may have an O-ring sealed door. The product or sample to be environmentally tested would be placed inside the sample chamber 102.

As shown in by the arrows in FIG. 1, the first blower 106 provides air circulation from the sample chamber 102, through the first temperature control chamber 104, through the humidity control chamber 108, through the first filter 110, through the second temperature control chamber 112 and back to the sample chamber 102. The air travels the air path from the sample chamber 102 immediately prior to entering the first temperature control chamber 104.

A relative humidity of sample chamber 102 may be controlled by the operation of the first temperature control chamber 104, the first blower 106, the humidity control chamber 108, the first filter 110, and the second temperature control chamber 112.

The first temperature control chamber 104 can raise or lower a temperature of the air leaving the sample chamber 102. The first temperature control chamber 104 is used to adjust the air temperature to a temperature needed by the humidity control chamber 108 as described below with reference to FIG. 3. The humidity control chamber 108 controls or dictates the relative humidity of the air. The second temperature control chamber 112 can raise or lower a temperature of the air coming from the humidity control chamber 108 and returning to the sample chamber 102, and is used to achieve a desired air temperature in the sample chamber 102.

The first temperature control chamber 104 is coupled to the sample chamber 102 and to the humidity control chamber 108. The second temperature control chamber 112 is coupled to the humidity control chamber 108. The fourth temperature control chamber 122 is coupled to the sample chamber 102 and to the pollutant chamber 114. The pollutant chamber 114 is coupled to the third temperature control chamber 120.

The first filter 110 helps to contain a saturated salt solution in the humidity control chamber 108. The first filter 110 material can be ordinary mechanical filtration, which can capture the salt particles coming off the saturated salt solution. The first filter 110 may be a series of one or more replaceable filters, and for example may be a minimum efficiency reporting value (MERV) filter rated MERV13.

A sulfur concentration of the sample chamber 102 may be controlled by the operation of the fourth temperature control chamber 122, the pollutant chamber 114, the second filter 116, the second blower 118 and the third temperature control chamber 120. As shown in by the arrows in FIG. 1, the second blower 118 provides air circulation from the sample chamber 102, through the fourth temperature control chamber 122, through the pollutant chamber 114, through the second filter 116, through the third temperature control chamber 120 and back to the sample chamber 102. The pollutant chamber 114 controls or dictates the pollutant concentration of the air and is described in more detail below with reference to FIGS. 5 and 6.

The second filter 116 helps to contain the pollutant in the pollutant chamber 114. The second filter 116 material can be ordinary mechanical filtration, which can capture pollutant particles coming off the pollutant chamber 114. The second filter 116 may be a series of one or more replaceable filters, and for example may be a minimum efficiency reporting value (MERV) filter rated MERV13.

Figure 2:
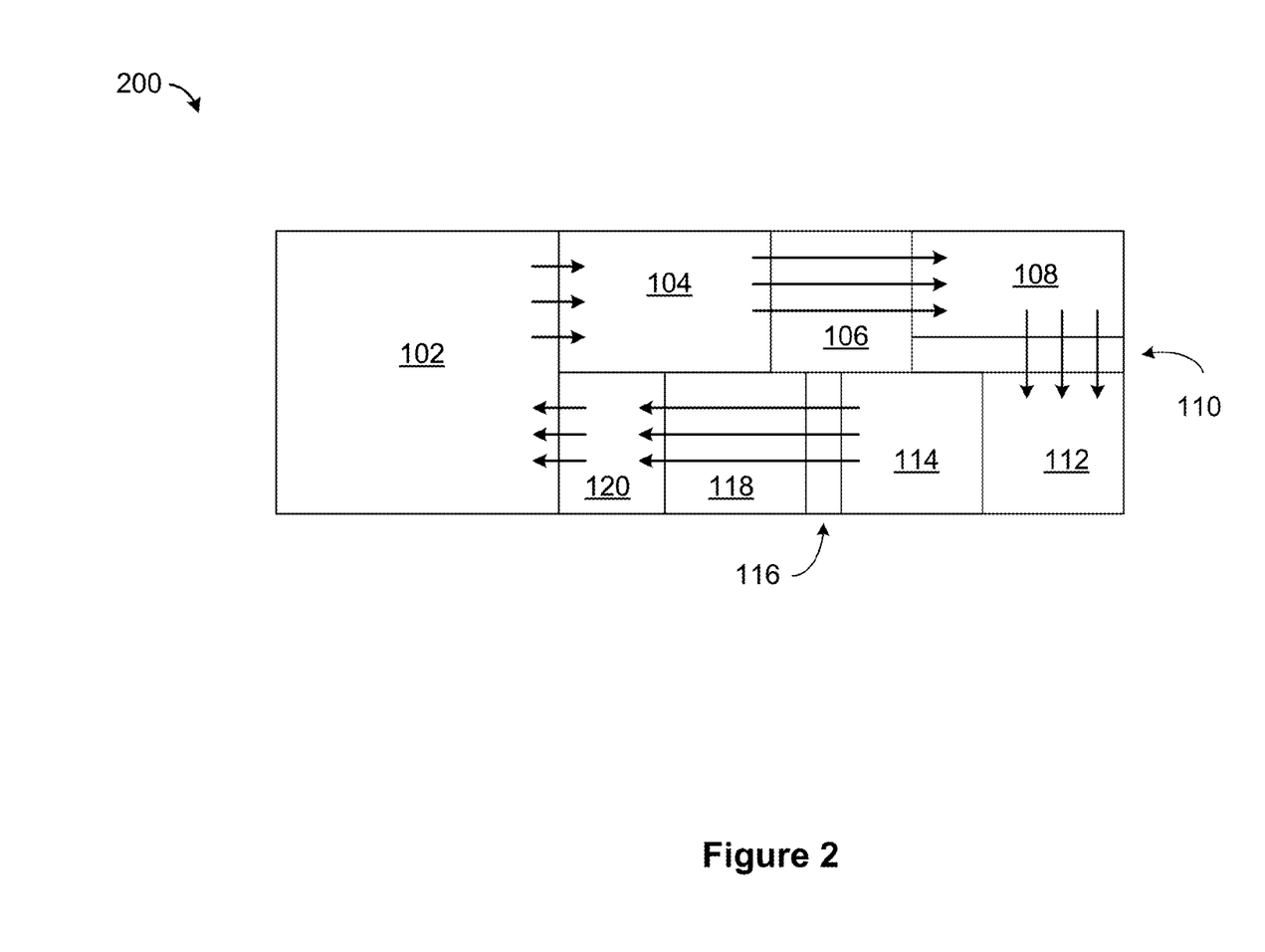
FIG. 2 is a cross-section view of an environmental test chamber, according to another exemplary embodiment.

Referring now to FIG. 2, an environmental sample chamber 200 according to another exemplary embodiment is shown. The environmental sample chamber 200 is substantially similar to the environmental test chamber 100. The components of environmental sample chamber 200 are substantially the same and operate as described above in the description for FIG. 1. As shown in FIG. 1, there is an air path circulating between the sample chamber 102 and the humidity control chamber 108, and there is an air path circulating between the sample chamber 102 and the pollutant chamber 114. As shown in FIG. 2, there is an air path circulating between the sample chamber 102, the humidity control chamber 108 and the pollutant chamber 114. The air path in FIG. 2 demonstrates that the air paths of FIG. 1 can be combined in an embodiment.

As shown in FIG. 2, as shown by the arrows, the first blower 106 and the second blower 118 provides air circulation from the sample chamber 102, through the first temperature control chamber 104, through the humidity control chamber 108, through the first filter 110, through the second temperature control chamber 112, through the pollutant chamber 114, through the second filter 116, through the third temperature control chamber 120 and back to the sample chamber 102.

Figure 3:
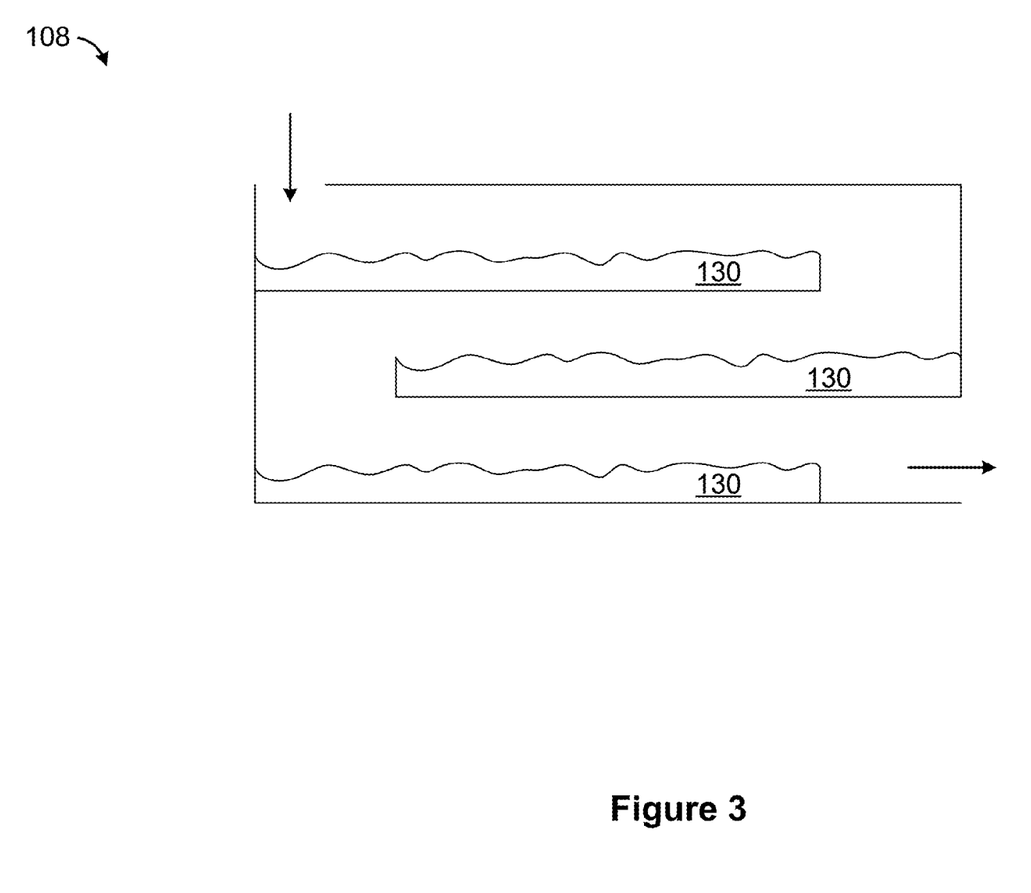
FIG. 3 is a cross-section view of a humidity control chamber, according to an exemplary embodiment.

Referring now to FIG. 3, the humidity control chamber 108 used to control the relative humidity of the air within the environmental test chamber 100, and more specifically within the sample chamber 102 is shown. The arrows show the air path into the humidity control chamber 108 and out of the humidity control chamber 108.

The humidity control chamber 108 includes three beds 130 containing a saturated salt solution. The beds 130 are configured in a labyrinth pattern to maximize contact between the saturated salt solution and the air passing through the humidity control chamber 108. Exposing the air to the saturated salt solution will affect the relative humidity of the air. The saturated salt solution may generally include a well-mixed solution of water and salt. In an embodiment, an excess of salt shall exist such that some salt remains on the bottom of the beds 130. In such cases, the saturated salt solution is fully saturated, and may be referred to a saturated salt solution. Adjusting the air temperature in the humidity control chamber 108 will control the relative humidity of the air.

In general, relative humidity is the amount of water present in the air, expressed as a percentage of the maximum amount of water the air can hold at a given temperature. Each saturated salt solutions in equilibrium with air above it with a unique relative humidity at a given air temperature. Thus, in the present case, the relative humidity of the air passing through the humidity control chamber 108 will depend on the air temperature and the particular salt used in the saturated salt solution. Stated differently, the specific salt used and the air temperature in the chamber will dictate relative humidity of the air in the humidity control chamber 108. The specific saturated salt solution used will be the main determinant of the relative humidity of the air; the relative humidity of the air in equilibrium with the saturated salt will be weakly dependent on the temperature of the chamber 108.

Examples of a saturated salt solution include magnesium chloride ($MgCl_2$), sodium chloride (NaCl), potassium chloride (KCl) and potassium sulfate ($K_2SO_4$). For example, at 60° C., magnesium chloride ($MgCl_2$) has a relative humidity of 30%, and sodium chloride (NaCl) has a relative humidity of 75%.

It should be noted that, while the embodiment depicted in the figures includes three beds 130 of the saturated salt solution; however, it will be understood by a person of ordinary skill in the art that any number of beds 130 may be included in the humidity control chamber 108 to achieve the desired result.

Figure 4:
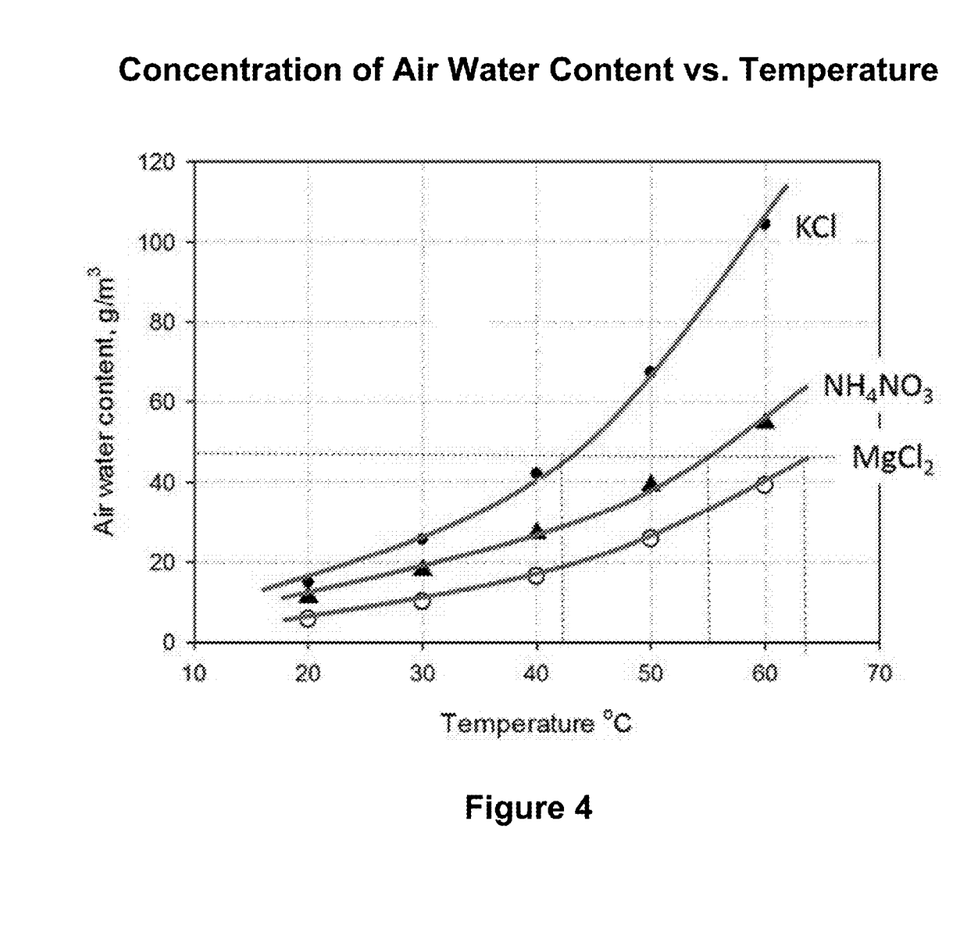
FIG. 4 is a graph of Air Water Content vs. Temperature.

Referring now to FIG. 4, a graph 400 is shown. The graph 400 is a graph of Air Water Content vs. Temperature in grams per meter cubed. There are 3 graph lines, one for each of: potassium chloride (KCl), aluminum nitrate ($NH_4NO_3$) and magnesium chloride ($MgCl_2$). Table 1 below of Humidity and Water Content in the 20-60° C. temperature range shows the data at points along the graph in FIG. 4.

TABLE 1

Humidity and Water Content in 20-60° C. temperature range

| Salt | | Temperature ° C. | | | | |
|---|---|---|---|---|---|---|
| | | 20 | 30 | 40 | 50 | 60 |
| KCl | Relative Humidity % | 86 | 84 | 82 | 81 | 80 |
| | Water content g/m³ | 14.92 | 25.59 | 42.06 | 67.38 | 104.30 |
| $NH_4NO_3$ | Relative Humidity % | 65 | 59 | 53 | 47 | 42 |
| | Water content g/m³ | 11.27 | 17.97 | 27.19 | 39.10 | 54.76 |
| $MgCl_2$ | Relative | 33 | 33 | 32 | 31 | 30 |

TABLE 1-continued

Humidity and Water Content in 20-60° C. temperature range

| Salt | Temperature ° C. | | | | |
|---|---|---|---|---|---|
| | 20 | 30 | 40 | 50 | 60 |
| Humidity % Water content g/m$^3$ | 5.72 | 10.05 | 16.41 | 25.79 | 39.11 |

In an example, the sample chamber 102 needs to be set to 60° C. and 80% relative humidity. By referring to Table 1, potassium chloride (KCl) saturated salt solution can be used in the humidity control chamber 108 at 60° C. to achieve the desired 80% relative humidity. In this example, the same temperature as in the sample chamber 102 can be used in the humidity control chamber 108.

In another example, the sample chamber 102 needs to be set to 40° C. and 90% relative humidity. The water content of air at 40° C. and 90% RH is 46 g/m$^3$. By referring to the graph 400 in FIG. 4, potassium chloride (KCl) saturated salt solution can be used at 42° C. in the humidity control chamber 108 to achieve the water content of air of 46 g/m$^3$, which will result in the desired 90% relative humidity at 40° C. in the sample chamber 102. Alternatively, aluminum nitrate ($NH_4NO_3$) saturated salt solution can be used at 55° C., or magnesium chloride ($MgCl_2$) saturated salt solution can be used at 64° C. in the humidity control chamber 108. The second temperature control chamber 112 will change the temperature of the air leaving the humidity control chamber 108 to 40° C. prior to entering the sample chamber 102. Cooling or heating the air does not change the water content of the air. The air returning to the sample chamber 102 will be 40° C. and 90% relative humidity.

Figure 5:
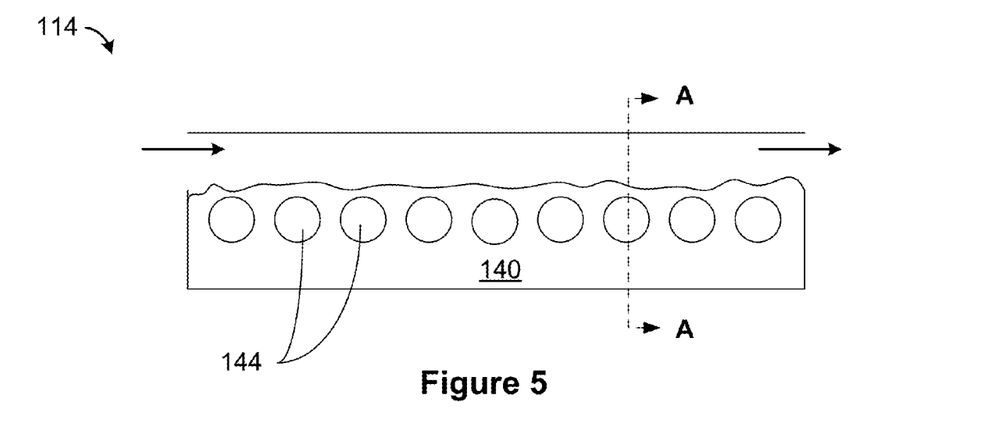
FIG. 5 is a cross-section view of a pollutant chamber, according to an exemplary embodiment.
Figure 6:
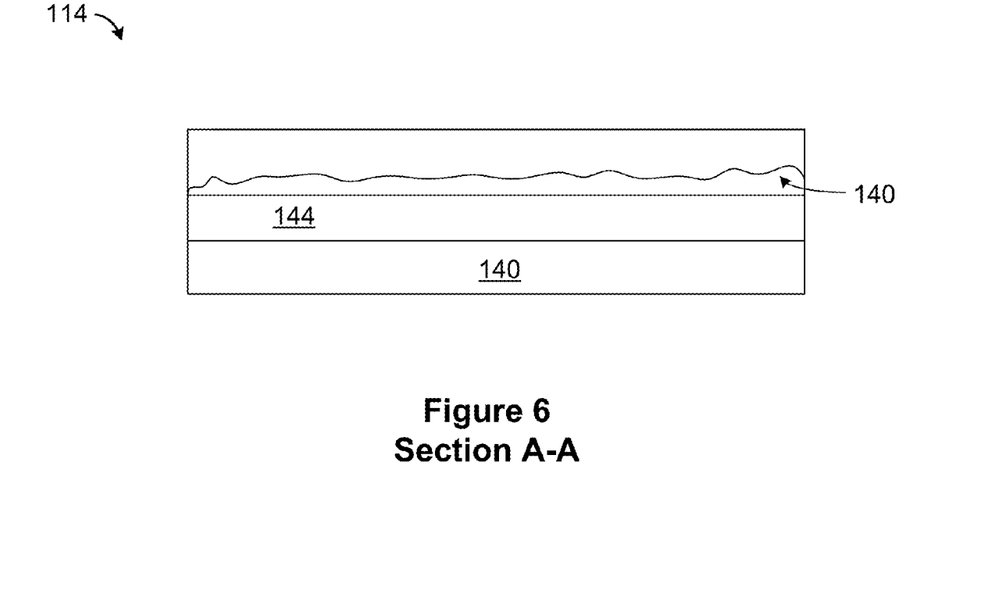
FIG. 6 is a cross section view of FIG. 5, along section line A-A.

Referring now to FIGS. 5 and 6, the pollutant chamber 114 is shown. The arrows show the air path into the pollutant chamber 114 and out of the pollutant chamber 114. The pollutant chamber has a sulfur bed 140 and a cooling tube 144. The cooling tube 144 is in direct contact with the sulfur. The cooling tube 144 may be one continuous tube or may be one or more tubes. The one or more cooling tubes 144 may be in series or in parallel. As the air circulates through the pollutant chamber 114, the air contacts the sulfur. The exposure of the air to the sulfur will control the sulfur concentration of the air. The concentration of the sulfur will depend on the temperature of the air. FIG. 6 is a cross section view of FIG. 5, along section line A-A.

Flower of sulfur (FOS) ($S_8$) is a fine yellow powered, pure form of sulfur produced by sublimation. Sulfur oxidizes most metals. Environmental testing results of creep corrosion on a circuit board caused by sulfur gas behaves similarly to creep corrosion of a circuit board in a computer data center, where the circuit board may be exposed to pollutants such as hydrogen sulfide ($H_2S$). The use of sulfur gas in the sample chamber 102 has yielded test results which correlate closely to field results of creep corrosion.

The cooling tube 144 can made from a material which is resistant to corrosion, such as titanium tubing or stainless steel tubing.

The concentration of sulfur in the air in a chamber containing the sulfur bed 140 is a function of a temperature of the cooling tube 144. To control the sulfur concentration in the sample chamber 102 independent of the air temperature in the sample chamber 102, the sulfur bed 140 is in the pollutant chamber 114. The cooling tube 144 may have a temperature set to a corresponding temperature dependent on the desired sulfur concentration in the sample chamber 102. When air is moved over the sulfur bed 140, the sulfur sublimes from the solid state to the gaseous state, becoming a vapor in the air. Controlling the temperature of the cooling tube 144 controls the concentration of the sulfur in the air.

Depending on the temperature of the cooling tube 144, the sulfur will either evaporate off the sulfur bed or condense on to the sulfur bed. If the sulfur content of the air is more than the concentration that would be in equilibrium with the sulfur bed, the sulfur will condense; if the sulfur content in the air is less than that would be in equilibrium with the sulfur bed, the sulfur will evaporate.

The air temperature of the sample chamber 102 must be higher than the air temperature of the cooling tube 144, to avoid condensation of sulfur in the sample chamber 102. If there is a surface in the sample chamber 102 or anywhere else in the air circulation which is at a lower temperature than the temperature of the cooling tube 144, this will cause sulfur condensation on the surface.

An example may be to have the sample chamber 102 set to 60° C. and 0.1 ppm sulfur concentration. A 0.1 ppm sulfur concentration corresponds to a 32.2° C. (90° F.) temperature of the cooling tube 144, per the chart 700 in FIG. 7, as described below. The chart 700 shows a temperature of approximately 90° F. which corresponds to 32.2° C. The air leaving the sample chamber 102 is at 60° C. and enters the pollutant chamber 114. The cooling tube 144 is set to 32.2° C. and the air circulating over the sulfur bed 140 cools down to 32.2° C. and therefore has a 0.1 ppm sulfur concentration. The pollutant chamber 114 will set the sulfur concentration to 0.1 ppm. The second filter 116 will remove excess sulfur from the air. The third temperature control chamber 120 will change the air temperature to 60° C. The air returning to the sample chamber 102 will be 60° C. and 0.1 ppm sulfur concentration. No surface in the chamber or any of the air circulation can have temperature less than 32.2° C. to avoid sulfur condensation.

Figure 7:
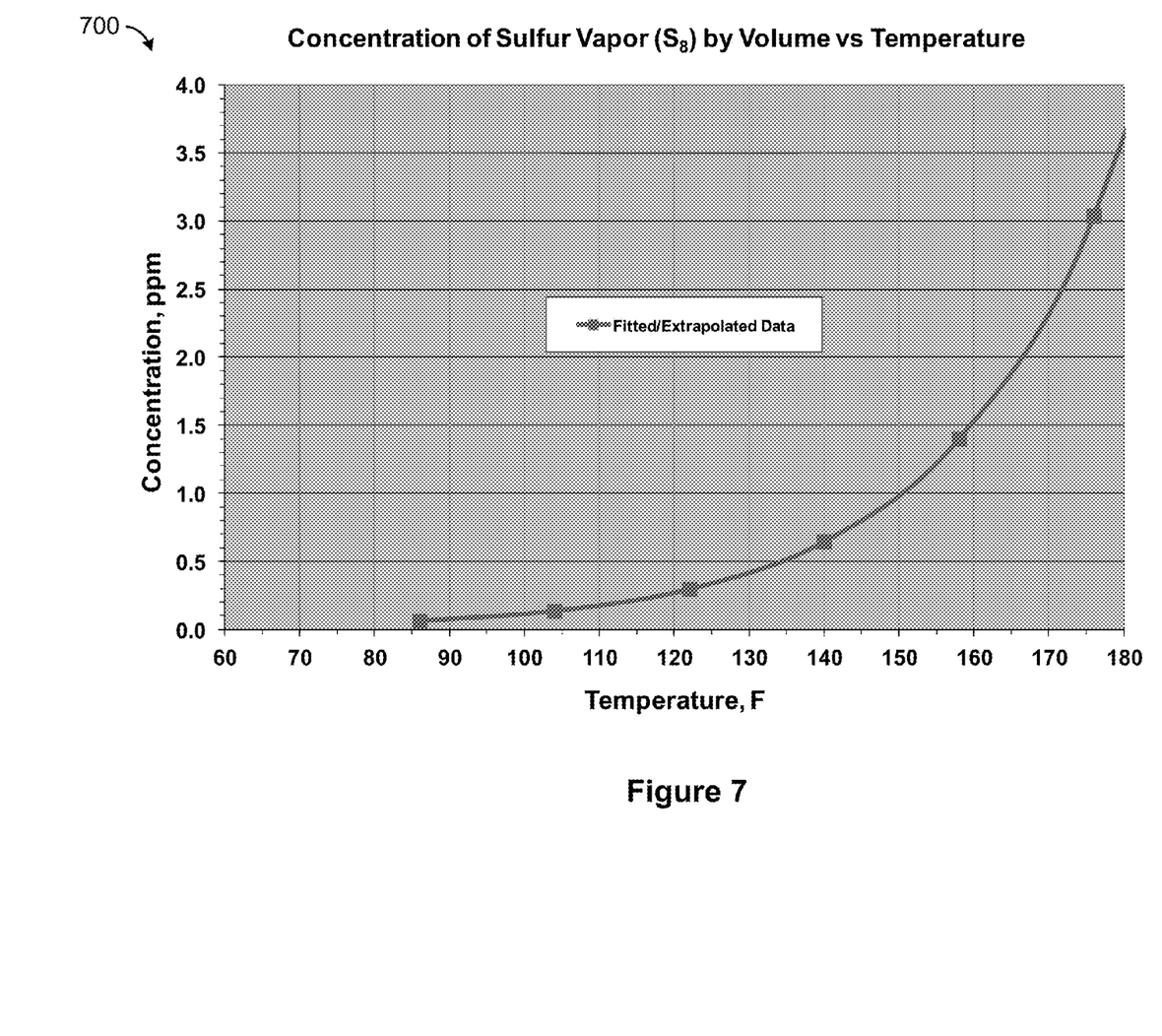
FIG. 7 is a graph of concentration of Sulfur Vapor (S8) by Volume vs. Temperature.

Referring now to FIG. 7, a graph 700 is shown. The graph 700 shows the concentration of Sulfur Vapor ($S_8$) by Volume vs Temperature. The x-axis shows Temperature in Fahrenheit. The y-axis shows concentration in part per million, ppm.

In an alternate embodiment, an additional pollutant may be introduced into the sample chamber 102 for environmental testing of the electronic component when exposed to an additional pollutant. For example, a beaker of Clorox®, which gives off chorine ($Cl_2$) gas, may be placed in the sample chamber 102.

The invention described above demonstrates the sample chamber 102 which has the humidity control chamber 108 and the pollutant chamber 114 with air circulation directly between the sample chamber 102 and the humidity control chamber 108, and air circulation between the pollutant chamber 114 and the sample chamber 102. The humidity control chamber 108 is attached to the sample chamber 102. The pollutant chamber 114 is attached to the sample chamber 102. The sample chamber 102 is simpler to build, easier to maintain and easier to control than the MFG chamber. The sample chamber 102 has control of the relative humidity and the sulfur concentration independent of air temperature. The sample chamber 102 provides an inexpensive means to control relative humidity in the 50%-90% range and sulfur concentration up to 4 ppm at 180° F. and higher sulfur concentrations at higher temperatures.

It may be noted that not all advantages of the present invention are include above.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. An environmental test chamber comprising:
   a sample chamber;
   a first temperature control chamber coupled to the sample chamber;
   a humidity control chamber coupled to the first temperature control chamber;
   a second temperature control chamber coupled to the humidity control chamber;
   a first blower circulating air sequentially from the sample chamber, through the first temperature control chamber, through the humidity control chamber, through the second temperature control chamber and back to the sample chamber;
   a fourth temperature control chamber coupled to the sample chamber;
   a pollutant control chamber coupled to the fourth temperature control chamber;
   a third temperature control chamber coupled to the pollutant chamber; and
   a second blower circulating air sequentially from the sample chamber, through the fourth temperature control chamber, through the pollutant control chamber, through the third temperature control chamber and back to the sample chamber.

2. The structure of claim 1, wherein the humidity control chamber comprises:
   a saturated salt solution in a labyrinth, wherein the circulated air contacts the saturated salt solution.

3. The structure of claim 2, wherein a temperature and a composition of the saturated salt solution dictates a relative humidity of the sample chamber.

4. The structure of claim 1, wherein the pollutant control chamber comprises:
   a bed of sulfur; and
   a cooling tube in direct contact with, and used to control a temperature of, the sulfur.

5. The structure of claim 4, wherein a temperature of the cooling tube dictates a concentration of sulfur in the air.

6. The structure of claim 1, wherein the sample chamber comprises two or more pollutants.

7. An environmental test chamber comprising:
   a sample chamber;
   a first air path beginning in the sample chamber and extending through a humidity control chamber, the first air path circulates air between the sample chamber and the humidity control chamber; and
   a second air path beginning in the sample chamber and extending through a pollutant control chamber, the second air path circulates air between the sample chamber and the pollutant control chamber.

8. The structure of claim 7, wherein the humidity control chamber comprises:
   a saturated salt solution in a labyrinth, wherein the circulated air contacts the saturated salt solution.

9. The structure of claim 8, wherein a temperature and a composition of the saturated salt solution dictates a relative humidity of the sample chamber.

10. The structure of claim 7, wherein the pollutant control chamber comprises:
    a bed of sulfur; and
    a cooling tube in direct contact with, and used to control a temperature of, the sulfur.

11. The structure of claim 10, wherein a temperature of the cooling tube dictates a concentration of sulfur in the air.

12. The structure of claim 7, wherein the sample chamber comprises two or more pollutants.

13. The structure of claim 7, wherein the first air path is separate and distinct from the second air path.

14. The structure of claim 7, wherein the first air path may at least partially coincide with the second air path.

* * * * *